US011235067B2

(12) United States Patent
Xu

(10) Patent No.: US 11,235,067 B2
(45) Date of Patent: Feb. 1, 2022

(54) NANOCOMPLEXES OF POLYANION-MODIFIED PROTEINS

(71) Applicant: Trustees of Tufts College, Medford, MA (US)

(72) Inventor: Qiaobing Xu, Lexington, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 16/479,344

(22) PCT Filed: Jan. 23, 2018

(86) PCT No.: PCT/US2018/012783
§ 371 (c)(1),
(2) Date: Jul. 19, 2019

(87) PCT Pub. No.: WO2018/140220
PCT Pub. Date: Aug. 2, 2018

(65) Prior Publication Data
US 2019/0381189 A1     Dec. 19, 2019

Related U.S. Application Data

(60) Provisional application No. 62/451,257, filed on Jan. 27, 2017.

(51) Int. Cl.
*A61K 47/69*     (2017.01)
*A61K 47/54*     (2017.01)
(Continued)

(52) U.S. Cl.
CPC .......... *A61K 47/6939* (2017.08); *A61K 38/45* (2013.01); *A61K 45/06* (2013.01);
(Continued)

(58) Field of Classification Search
CPC ................................................. A61K 47/6939
See application file for complete search history.

(56) References Cited

U.S. PATENT DOCUMENTS

| 2016/0082126 A1 | 3/2016 | Xu et al. |
| 2016/0129120 A1 | 5/2016 | Xu et al. |
| 2019/0381189 A1 | 12/2019 | Xu |

FOREIGN PATENT DOCUMENTS

| WO | WO-0105434 A2 * | 1/2001 | ............. A61K 47/61 |
| WO | WO-2014186348 A2 * | 11/2014 | ............... A61K 9/16 |

OTHER PUBLICATIONS

M Wang, K Alberti, S Sun, CL Arellano, Q Xu. "Combinatorially Designed Lipid-like Nanoparticles for Intracellular Delivery of Cytotoxic Protein for Cancer Therapy." Angewandte Chemie International Edition, vol. 53, 2014, pp. 2893-2898, published online Feb. 12, 2014. (Year: 2014).*

(Continued)

*Primary Examiner* — Isaac Shomer
(74) *Attorney, Agent, or Firm* — Foley Hoag LLP; Dana M. Gordon; Alexander J. Chatterley

(57) ABSTRACT

A nanocomplex, 50 to 1000 nm in size, containing a lipid-like nanoparticle formed of a cationic lipid-based compound and a modified protein formed of a protein and an anionic polymer that includes a plurality of polar groups, the lipid-like nanoparticle and the modified protein being non-covalently bonded to each other. Also disclosed are a method of preparing the above-described nanocomplex and use thereof for treating a medical condition. Further disclosed is a pharmaceutical composition containing a nanocomplex.

12 Claims, 2 Drawing Sheets

(51) Int. Cl.
*B82Y 5/00* (2011.01)
*A61K 47/61* (2017.01)
*A61K 38/45* (2006.01)
*A61K 45/06* (2006.01)

(52) U.S. Cl.
CPC ............ *A61K 47/543* (2017.08); *A61K 47/61* (2017.08); *A61K 47/6907* (2017.08); *B82Y 5/00* (2013.01)

(56) References Cited

OTHER PUBLICATIONS

G Mattheolabakis, L Milane, A Singh, MM Amiji. "Hyaluronic acid targeting of CD44 for cancer therapy: from receptor biology to nanomedicine." Journal of Drug Targeting, vol. 23(7-8), 2015, pp. 605-618, published online Oct. 5, 2015. (Year: 2015).*

Alisa L. Becker, Nicole Welsch, Christian Schneider, and Matthias Ballauff. "Adsorption of RNase A on Cationic Polyelectrolyte Brushes: A Study by Isothermal Titration Calorimetry." Biomacromolecules, vol. 12, 2011, pp. 3936-3944. (Year: 2011).*

Wang et al. "Hyaluronic acid modification of RNase A and its intracellular delivery using lipid-like nanoparticles." Journal of Controlled Release, vol. 263, 2017, pp. 39-45. (Year: 2017).*

Wang et al., "Hyaluronic acid modification of RNase A and its intracellular delivery using lipid-like nanoparticles," Journal of Controlled Release, 263:39-45 (2018).

International Search Report and Written Opinion for International Application No. PCT/US2018/012783 dated May 7, 2018.

Mero et al., "Hyaluronic acid bioconjugates for the delivery of bioactive molecules," Polymers, 6(2):346-369 (2014).

Figueroa et al., "Induction of cancer cell death by Hyaluronic acid-mediated uptake of Cytochrome C," Journal of Nanomedicine and Nanotechnology, 6(5): (2015).

So et al., "Situation of Monomethoxypolyethylene Glycol Covalently Attached to Lysozyme," J. Biochem., 119: 1086-1093 (1996).

Treetharnmathurot et al., "Effect of PEG molecular weight and linking chemistry on the biological activity and thermal stability of PEGylated trypsin," International Journal of Pharmaceutics, 357: 252-259 (2008).

* cited by examiner

NANOCOMPLEXES OF POLYANION-MODIFIED PROTEINS

RELATED APPLICATIONS

This application is the U.S. national phase of International Patent Application No. PCT/US2018/012783, filed Jan. 23, 2018, which claims the benefit of U.S. Provisional Patent Application No. 62/451,257, filed Jan. 27, 2017.

This invention was made with government support under grant 1452122 awarded by the National Science Foundation. The government has certain rights in the invention.

GOVERNMENT SUPPORT

This invention was made with government support under grant 1452122 awarded by the National Science Foundation. The government has certain rights in the invention.

BACKGROUND

Protein-based therapeutics have received great attention due to their high specificity and low off-target effects. They are widely used for treating various medical conditions, including cancer, infection, diabetes, inflammation, and degenerative diseases.

Currently, most protein-based drugs treat diseases by targeting cell surface ligands or extracellular domains. Use of protein drugs to target intracellular sites remains a significant challenge as the cell membrane is largely impermeable to proteins.

Target-specific delivery systems have been developed for transporting protein-based therapeutics into cells to target a specific site. See Place et al., Molecular Therapy-Nucleic Acids, 1, e15 (2012). Examples of the delivery systems include polymers and inorganic nanoparticles. See Gonzles-Toro et al., Journal of American Chemical Society, 134, 6964-67 (2012). Yet, when delivering protein drugs, these systems do not produce desired therapeutic effects as proteins are not readily released into the cells effectively. See Brown, Expert Opinion on Drug Delivery, 2, 29-42 (2005).

There is a need to develop a new system that efficiently delivers a protein-based therapeutic to its intracellular target site.

SUMMARY

An aspect of the present invention is a nanocomplex that effectively transports proteins into cells to exert therapeutic effects. It contains (i) a lipid-like nanoparticle formed of a cationic lipid-based compound and (ii) a modified protein formed of a protein and an anionic polymer containing a plurality of polar groups, each being $CO_2H$, $CO_2^-$, $SO_3H$, $SO_3^-$, $PO_3H$, or $PO_3^-$. The lipid-like nanoparticle binds to the modified protein via non-covalent interaction to form the nanocomplex, which has a particle size of 50 to 1000 nm.

Typically, the cationic lipid-based compound is formed from an electrophile and an amine. The electrophile can be an epoxide, an acrylate, or an acrylamide and the amine can be a primary or secondary amine Examples of the protein include a protein-based cytotoxin, an antibody, a transcription factor, or a genome-editing protein; and examples of the anionic polymer include hyaluronic acid, heparin, DNA, RNA, polysialic acid, polyglutamic acid, pentosan polysulfate sodium, sulphated polysaccharide, negatively charged serum albumin, negatively charged milk protein, synthetic sulphated polymer, polymerized anionic surfactant, or polyphosphate.

Another aspect of this invention is a method of preparing the nanocomplex described above. The method includes the following steps: activating an anionic polymer that contains a plurality of polar groups, the polar groups being $CO_2H$, $CO_2^-$, $SO_3H$, $SO_3^-$, $PO_3H$, or $PO_3^-$; conjugating the activated anionic polymer to a protein via covalent bonding to form a modified protein; obtaining a lipid-like nanoparticle formed of a cationic lipid-based compound; and finally bonding the lipid-like nanoparticle to the modified protein to form a nanocomplex having a particle size of 50 to 1000 nm.

A still further aspect of this invention is a pharmaceutical composition containing a nanocomplex thus prepared and a pharmaceutically acceptable carrier thereof.

Finally, this invention further covers a method of using the above-described nanocomplex for treating a medical condition in a subject, in which the protein contained in the nanocomplex, upon delivery into cells, is released and exerts a therapeutic effect on the medical condition.

The details of the invention are set forth in the description below. Other features, objects, and advantages of the invention will be apparent from the following drawings and detailed description of several embodiments, and also from the appending claims.

DETAILED DESCRIPTION

Figure 1:
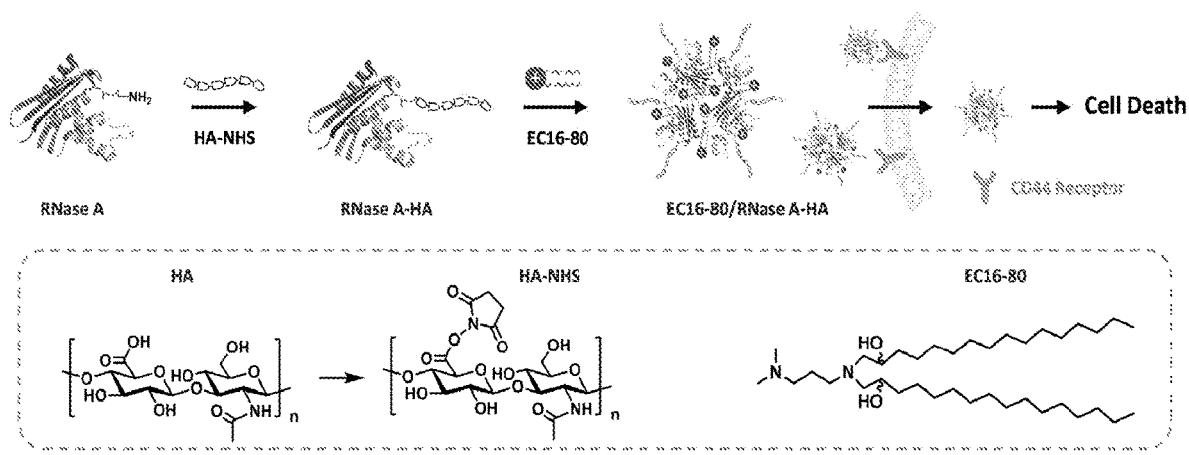
FIG. 1 is a schematic depiction of (i) synthesis of a nanocomplex containing hyaluronic acid (HA)-modified RNase A and a cationic lipid-based compound, i.e., EC16-80; and (ii) targeted delivery of protein RNase A into CD44 over-expressing cells.

Disclosed first in detail herein is a nanocomplex that can be used to deliver a protein-based therapeutic into cells.

To reiterate, the nanocomplex contains a lipid-like nanoparticle and a modified protein formed of a protein and an anionic polymer, the lipid-like nanoparticle bound to the modified protein via non-covalent interaction to form a nanocomplex having a particle size of 50 to 1000 nm. The lipid-like nanoparticle is formed of a cationic lipid-based compound. On the other hand, the anionic polymer contains a plurality of polar groups.

The cationic lipid-based compound can be prepared by reacting an electrophile with an amine, the electrophile being an epoxide, an acrylate, or an acrylamide and the amine being a primary or secondary amine.

The epoxide, acrylate, or acrylamide can contain a $C_1$-$C_{20}$ alkyl or $C_1$-$C_{20}$ heteroalkyl group. Examples include, but are not limited to,

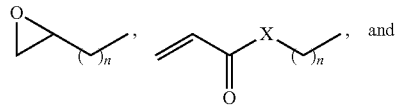

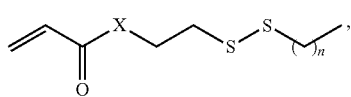

in which X is O or NH and n is 9-17.

Shown below are examples of the primary or secondary amine:

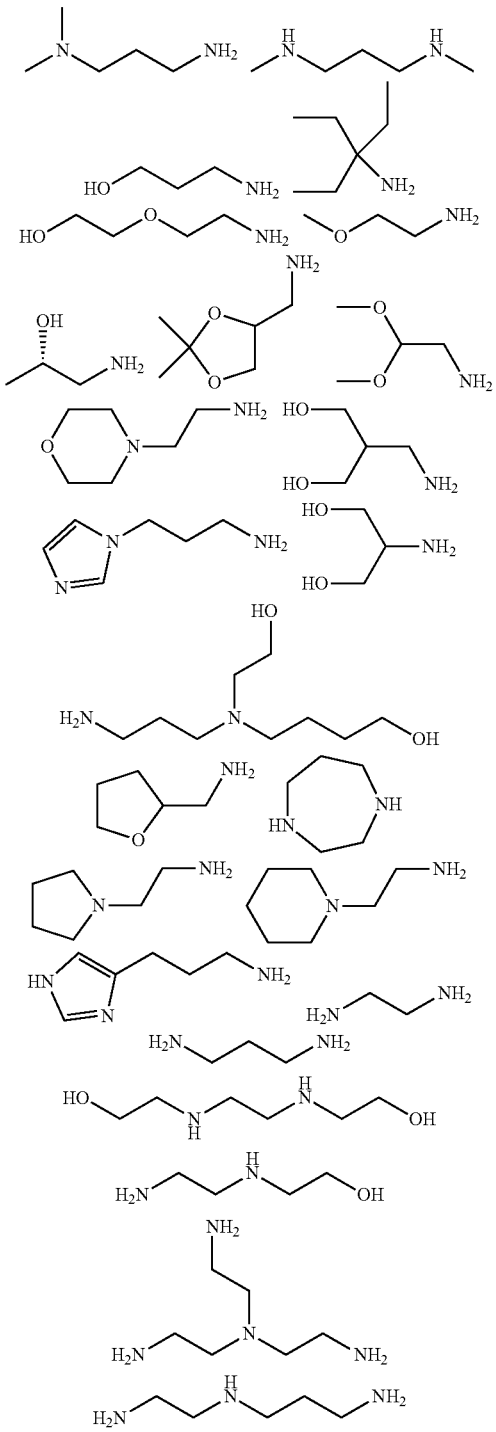

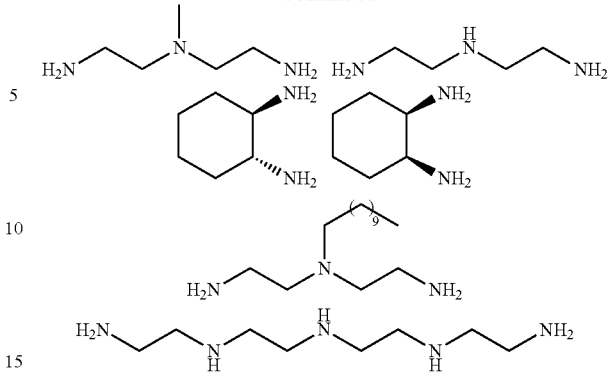

The term "alkyl" refers to a saturated, linear or branched hydrocarbon moiety, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, and triacontyl.

The term "heteroalkyl" herein refers to an alkyl moiety containing at least one heteroatom selected from N, O, P, B, S, Si, Sb, Al, Sn, As, Se, and Ge.

Unless specified otherwise, both alkyl and heteroalkyl mentioned herein include both substituted and unsubstituted moieties.

The protein contained in the nanocomplex can be a protein-based cytotoxin (e.g., RNase, saporin, gelonin, ricin chain A, shiga toxin chain Al, or botulinum neurotoxin), an antibody, a transcription factor, or a genome-editing protein (e.g., Cas9 or Cpf1).

The anionic polymer used to modify the protein is typically one of the following: hyaluronic acid, heparin, DNA, RNA, polysialic acid, polyglutamic acid, pentosan polysulfate sodium, sulphated polysaccharide, negatively charged serum albumin, negatively charged milk protein, synthetic sulphated polymer, polymerized anionic surfactant, and polyphosphate. It should be pointed out that a protein can be modified with one or more anionic polymers, of which increased charge density on the modified protein facilitates the process of complexing it with a lipid-like nanoparticle via non-covalent interaction (e.g., electrostatic interaction) to form a nanocomplex.

In one embodiment of the nanocomplex described above, the cationic lipid-based compound is formed from an epoxide substituted with $C_1$-$C_{20}$ alkyl or $C_1$-$C_{20}$ heteroalkyl and a primary or secondary amine, the protein is a protein-based cytotoxin, an antibody, a transcription factor, or a genome-editing protein, and the anionic polymer is hyaluronic acid, heparin, DNA, RNA, polysialic acid, polyglutamic acid, pentosan polysulfate sodium, sulphated polysaccharide, negatively charged serum albumin, negatively charged milk protein, synthetic sulphated polymer, polymerized anionic surfactant, or polyphosphate.

An exemplary nanocomplex contains a lipid-like nanoparticle formed of a cationic lipid-based compound, and a modified protein formed of a protein and an anionic polymer, in which the cationic lipid-based compound is obtained from

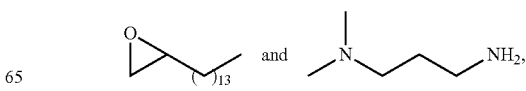

the protein is RNase, and the anionic polymer is hyaluronic acid.

Also within the scope of this invention is a method of preparing the nanocomplex described above. The method includes four steps: (i) activating an anionic polymer that contains a plurality of polar groups, the polar groups being $CO_2H$, $CO_2^-$, $SO_3H$, $SO_3^-$, $PO_3H$, or $PO_3^-$; (ii) conjugating the activated anionic polymer to a protein via covalent bonding to form a modified protein; (iii) obtaining a lipid-like nanoparticle formed of a cationic lipid-based compound; and (iv) bonding the lipid-like nanoparticle to the modified protein to form a nanocomplex.

The nanocomplex thus obtained has a particle size of 50 to 1000 nm (e.g., 50 to 500 nm, 50 to 300 nm, and 50 to 140 nm).

Further covered by this invention is a pharmaceutical composition containing a nanocomplex thus prepared and a pharmaceutically acceptable carrier thereof. The pharmaceutical carrier is compatible with the nanocomplex and should not be deleterious to a subject to be treated.

Still within the scope of this invention is a method of using the nanocomplex thus prepared for treating a medical condition in a subject, the method including administering to the subject in need thereof an effective amount of a nanocomplex, in which the protein contained in the nanocomplex, upon delivery into cells, is released and exerts a therapeutic effect on the medical condition.

"An effective amount" herein refers to the amount of the nanocomplex that is required to confer a therapeutic effect on the treated subject, e.g., inhibition of cancer cells growth. Effective doses will vary, as recognized by those skilled in the art, depending on the types of medical uses (i.e., treatment of cancer), route of administration, excipient usage, and the possibility of co-usage with other medical treatment.

The nanocomplex of this invention can be used in treating various medical conditions, e.g., cancer. Examples of the cancer include, but are not limited to, breast cancer, prostate cancer, ovarian cancer, or leukemia.

In one embodiment, the nanocomplex is used to treat a medical condition, in which cells associated with the medical condition have high CD44 expression.

Shown in FIG. 1 below is an illustration of using a nanocomplex of this invention for targeting CD44 overexpressing cells.

First, anionic polymer hyaluronic acid (HA) is activated with N-hydroxyl succinimide (NHS) to form an activated anionic polymer, i.e., HA-NHS, which is subsequently conjugated to protein RNase A to afford a modified protein, i.e., RNase A-HA. Next, a cationic lipid-based compound (EC16-80; structure shown in FIG. 1) is used to form a lipid-like nanoparticle, which is complexed with the modified protein to obtain a nanocomplex, i.e., EC16-80/RNase A-HA. Finally, targeted intracellular delivery is performed to convey the nanocomplex thus obtained into CD44 overexpressing cells, e.g., A549 cells, thereby releasing RNase A to cause cell death.

It should be pointed out that the HA modification plays two important roles:
(i) conjugation of HA to protein RNase A "cages" the primary amine groups of the lysine residues exposed on the protein surface, thereby increasing the negative charge density of the protein and facilitating its electrostatic complexation with the lipid-like nanoparticle; and
(ii) HA specifically binds to CD44 receptor, which is overexpressed on the cell surface of solid tumors, and, as such, HA conjugation to RNase A offers great potential for targeted cancer therapy.

A protocol of using nanocomplexes for treating cancer is described in Wang et al., Angew. Chem., 126, 2937-2942 (2014).

To practice the method of the present invention, a composition having the above-described nanocomplex can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or di-glycerides). Fatty acid, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition containing the nanocomplex can also be administered in the form of suppositories for rectal administration.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. The publications cited herein are incorporated by reference in their entirety.

Provided below are materials and methods used for preparing, characterizing, or utilizing the nanocomplexes of this invention, which are described in EXAMPLES 1-4 also below.

Materials

Unless noted otherwise, all chemicals for lipidoid (i.e., a cationic lipid-like compound) synthesis and protein modification were purchased from Sigma-Aldrich or Alfa-Aesar and used directly. Bovine pancreatic ribonuclease A (RNase A) was purchased from Sigma-Aldrich. Hyaluronic acid (Research Grade) was purchased from Life Core Biomedical. 1-Ethyl-3-(3-diemthylaminopropyl) carbodiimide (EDC) and N-hydroxyl succinimide (NHS) were purchased from Sigma-Aldrich. Protein activity of RNase A and RNase A-HA were measured using RNaseAlert® Kit (Integrated DNA Technologies, Inc., IA). Lipidoid EC16-80 was synthesized through the ring-opening reaction of 1,2-epoxyoctadecane and N,N-dimethyl-1,3-propanediamine according to literature reports. For example, see Altmoglu at el., Nanomedicine, 2015, 10, 643-657. Bicinchoninic acid (BCA) protein assay reagents were purchased from Thermo Scientific. Commercially available lipids used for lipidoid/protein nanocomplex formulations (DOPE and C16-PEG2000-ceramide) were purchased from Avanti Polar Lipid, Inc. Monoclonal anti-CD44 antibody was purchased from Sigma-Aldrich (C7923).

Cell Lines and Cell Culture

Human breast adenocarcinoma (MCF-7) cells with low CD44 expression and human lung adenocarcinoma epithelial (A549) cells with high CD44 expression were purchased from ATCC (Manassas, Va., USA). All cell lines were cultured in Dulbecco's modified Eagle's medium (DMEM; Sigma-Aldrich) supplemented with 10% FBS (Sigma-Aldrich) and 1% penicillin-streptomycin (Life Technologies) under an atmosphere of 5% $CO_2$/air at 37° C.

BCA Test and SDS-PAGE Analysis

The protein concentration of RNase A-HA was determined using a Pierce BCA protein assay kit (Thermo Scientific Cat. No. 23227) according to the manufacturer's instructions. SDS-PAGE analysis was conducted also according to the manufacturer's instructions using 4-12% Bis-Tris gel (NuPAGE) and Colloidal Blue Staining Kit (Invitrogen, Cat. No. LC6025).

MALDI-TOF Mass Spectrometry

Matrix-assisted laser desorption/ionization time-of-flight (MALDI-TOF) mass spectrometry was employed to analyze the molecular weights of protein before and after the chemical modification, RNase A and RNase A-HA. Samples were prepared by mixing 1 μL, of protein solution (1 mg/mL) with 9 μL of matrix solution (saturated sinapinic acid in 50/50 acetonitrile/water with 0.1% trifluoroacetic acid (TFA)).

$^1$H NMR Analysis

Compositions of HA, RNase A, and RNase A-HA were characterized by $^1$H NMR analysis, using $D_2O$ as the solvent and a Bruker AVIII 500 MHz NMR spectroscopy.

Protein Activity Assay

Protein activities of RNase A and RNase A-HA were measured via the RNaseAlert® Kit according to the manufacturer's instructions. Briefly, 5 μL RNaseAlert® Substrate and 10 μL assay buffer (provided by the assay kit) were pre-mixed in a 96-well plate. To the above assay substrate, 85 μL of RNase A or RNase A-HA (2 ng/mL) was added. Fluorescence intensity of the protein-containing substrate was monitored within 25 minutes at 520 nm (excited at 490 nm).

Lipidoid Nanoparticle Formulation

Lipidoid/protein (EC16-80/RNase A and EC16-80/RNase A-HA) nanocomplexes were formulated by a reported thin film hydration method. See Wang et al., Angew. Chem., 2014, 126, 2937-2942. Briefly, lipidoid EC16-80 was mixed with cholesterol and DOPE (Avanti Polar Lipids) at a weight ratio of 16/4/1 (EC16-80/cholesterol/DOPE) and dissolved in chloroform. The chloroform was evaporated under vacuum condition, and further dried to form a thin film at the bottom of the vial. The thin film was then hydrated with a mixed solution of ethanol/sodium acetate buffer (200 mM, pH=5.2, v/v=9/1). The solution thus formed was subsequently added dropwise to an aqueous solution of C16-PEG2000-ceramide (Avanti Polar Lipids; EC16-80/C16-PEG2000-ceramide=16/1, w/w). The resulting solution was incubated at 37° C. for 30 minutes before dialysis (MWCO 3,500 Da) against PBS to obtain a lipidoid nanoparticle solution, which was then mixed with RNase A or RNase A-HA in PBS (25 mM, pH=7.4) at a predetermined weight ratio to prepare formulated lipidoid/protein nanocomplexes, e.g., EC16-80/RNase A.

Synthesis of FITC-Labeled Protein

RNase A-HA and RNase A were labeled with fluorescein isothiocyanate (FITC) for cellular uptake study. Briefly, 2 mg of protein (RNase A-HA or RNase A) was dissolved in 750 μL of 0.1 M $NaHCO_3$ buffer solution (pH=9.5), and mixed with 250 μL freshly prepared FITC solution (4 mg/mL in DMSO). The reaction mixture was protected from light and stirred at room temperature for additional 2 hours, followed by ultrafiltration using Amicon® Ultra Centrifugal Filters (MWCO 10,000 Da, Millipore, Mass.) to remove impurities.

In Vitro Cytotoxicity Assay

MTT (i.e., 3-(4,5-dimethylthiazol-2-yl)-2,5-diphenyltetrazolium bromide) assay was employed to evaluate the cytotoxicity of free protein and lipidoid/protein nanocomplexes. Briefly, 100 μL of A549 or MCF-7 cell suspension was added into 96-well cell culture plates at a density of 5,000 cells per well, and incubated for 24 h at 37° C. in 5% $CO_2$ prior to transfection. The cells were then incubated with free RNase A-HA, blank EC16-80 nanoparticles, formulated EC16-80/RNase A, and EC16-80/RNase A-HA (with different lipidoid/protein weight ratios) at different protein concentrations for 48 hours. Cell viability was determined by the MTT assay. The absorbance was measured at 570 nm using a microplate reader. All experiments were performed in quadruplicate.

Effect of CD44 Receptor Blocking on Cytotoxicity

A549 cells (high CD44 expression) and MCF-7 cells (low CD44 expression) were incubated with anti-CD44 antibody (2 μg/mL) for 2 hours prior to transfection. The cells were then washed with PBS and placed back into fresh culture medium. The lipidoid/protein nanocomplexes described above were added to the cell culture medium. After 48-h incubation, cell viability was measured by MTT assay. All experiments were performed in quadruplicate.

Flow Cytometry Analysis

Free FITC-RNase A-HA, formulated EC16-80/FITC-RNase A and EC16-80/FITC-RNase A-HA were incubated with A549 and MCF-7 cells for 2 hours, with or without pretreatment of anti-CD44 antibody. Cellular uptake efficacies were then analyzed by flow cytometry. More specifically, A549 and MCF-7 cells were initially seeded for 24 hours at a density of 150,000 cells per well in 12-well cell culture plates. Formulated EC16-80/protein nanoparticles were prepared by mixing FITC-labeled RNase A (FITC-RNase A) or RNase A-HA (FITC-RNase A) in DMEM at a weight ratio of 2/1 (lipidoid/protein), followed by an additional 15 minutes of incubation at room temperature protected from light. The cells were washed twice with PBS buffer and replaced with fresh DMEM (700 μL per well). Free proteins or lipidoid/protein nanoparticles were then added. After 6-h of incubation at 37° C., the cell culture medium was removed, and cells were washed with 2 mL of 0.1% heparin in PBS, followed by PBS. Cells were then harvested using 0.25% (w/v) trypsin solution and dispersed in 0.4 mL of PBS for immediate flow cytometry analysis using a BD FACS Calibur (BD Science, CA).

In Vitro Fluorescent Cell Imaging

To perform a confocal laser scanning microscopy (CLSM) imaging, A549 cells were seeded in a BDFalcon™ 4-well culture slide at a density of 20,000 cells per well, 24 hours before the experiment. Then a fluorescent dye labeled lipidoid/protein nanocomplex was added into the cells culture medium and incubated for another 6 hours. Cells were washed twice using PBS buffer, and stained with 4',6-diamidino-2-phenylindole. CLSM images were captured on Leica TCS-SP5 (Leica Microsystems).

Example 1: Synthesis and Characterization of Hyaluronic Acid (HA) Modified RNase A HA modified RNase A (RNase A-HA) was prepared and characterized following the procedure described below.

Hyaluronic acid succinimidyl succinate (HA-NHS) was first obtained by activating HA with EDC and NHS in a molar ratio of 1/5.73/3.6 (HA/EDC/NHS) in de-ionized (DI) water. RNase A-HA was then prepared by reacting RNase A with an excess of HA-NHS as follows. The pH value of the reaction mixture was maintained at 4.7 by addition of 0.1 M NaOH/0.1 M HCl. The reaction was allowed to proceed for 24 hours at room temperature under a continuous stirring condition. After 24-h, the pH was adjusted to 7.4 with 0.1 M NaOH/0.1 M HCl and RNase A was added into the reaction solution to have a HA-NHS/RNase A molar ratio of 5:1. The reaction mixture thus formed was then maintained with continuous stirring at pH 7.5 at room temperature for 24 hours to afford final product RNase A-HA, which was purified by dialysis (MWCO 15,000 Da) using DI water at 4° C. for 3 days, then subjected to analysis with BCA, SDS-PAGE, MALDI-TOF, and $^1$H NMR, and enzyme activity assays, as described above.

The final product, RNase A-HA, was characterized by SDS-PAGE, MALDI-TOF, and $^1$H NMR. Due to the increase in molecular weight and decrease in charge density, it was observed that RNase A-HA showed a lagging band, as compared to unmodified RNase A. MALDI-TOF mass spectrometry showed that the molecular weight of RNase A-HA was increased by about 2,000 Da, as compared to native RNase A (13.7 kDa), indicating that one HA molecule was conjugated to protein RNase A, taking the molecular weight of HA (2247 Da) into account. $^1$H NMR analysis confirmed the presence of HA moieties contained in RNase A-HA, as the characteristic proton signals of HA were observed in the $^1$H NMR spectrum of RNase A-HA, as compared to unmodified RNase A. Additionally, enzyme activities of RNase A-HA and RNase A were measured by a commercially available RNase A kit. It was observed that RNase A-HA remained active although the enzyme activity was slightly decreased by ~15%, as compared to native RNase A.

Example 2: Preparation and Characterization of Protein-Loaded Nanocomplexes

Nanocomplexes containing RNase A or RNase A-HA and a lipidoid (i.e., a cationic lipid-based compound) were prepared and characterized following the procedure described below.

A lipidoid ("EC16-80") was prepared according to the method reported in Sun et al., Bioconjugate Chem., 2012, 23, 135-140.

Nanocomplexes formed from EC16-80 and a protein (RNase A or RNase A-HA) were obtained by using a thin film hydration method reported in Wang et al., Angew. Chem., 2014, 126, 2937-2942. Briefly, EC16-80, cholesterol, and DOPE were mixed at a weight ratio of 16:2:1 in chloroform, and the chloroform was then evaporated under vacuum to form a thin layer film. The thin layer film thus obtained was re-hydrated with phosphate-buffered saline, followed by addition of RNase A or RNase A-HA at a weight/weight ratio of 8:1 (EC16-80: protein) and incubation for 30 minutes at room temperature to afford EC16-80/ protein nanocomplexes.

Shown in Table 1 below are hydrodynamic size ($D_h$), zeta-potential, and protein loading efficiency of pure nanoparticle (lipidoid) and lipidoid/protein nanocomplexes. $D_h$ and zeta-potential were determined according to literature reports. For example, see Ahn et al., Scientific Reports 3, Article number: 1997 (2013).

TABLE 1

Hydrodynamic size, zeta-potential, and protein loading efficiency of lipidoid and lipidoid/protein nanoparticles.

| Nanocomplex | $D_h$ (nm) | Zeta-potential (mV) | Protein loading efficiency (%) |
|---|---|---|---|
| EC16-80 | 153.0 ± 3.6 | 24.2 ± 2.8 | / |
| EC16-80/RNase A | 141.3 ± 3.2 | 5.4 ± 2.4 | 80.3 |
| EC16-80/RNase A-HA | 134.5 ± 2.7 | −21.5 ± 3.5 | 92.7 |

As shown in Table 1, the averaged $D_h$ of EC16-80/RNase A-HA nanocomplex was found to be about 134.5 nm, identical to the size observed in a TEM image analysis. Unexpectedly, the size of EC16-80/RNase A-HA nanocomplex was smaller than that of EC16-80/RNase A (about 141.3 nm) and that of pure nanoparticle EC16-80 (about 153.0 nm).

The differences in hydrodynamic size of the pure nanoparticle and protein loaded nanocomplexes indicate that binding the cationic lipidoid nanoparticle with protein (RNase A or RNase A-HA) compressed the pure nanoparticle. The EC16-80/RNase A-HA nanoparticles had the densest and most compact nanostructure, possibly resulting from increased charge density of the modified protein.

Furthermore, charge density on the protein surface influences the zeta-potential of a lipidoid/protein nanocomplex. As shown in Table 1 above, the zeta-potential of pure lipidoid nanoparticle (EC16-80) was about 24.2 mV and, by contrast, complexation with RNase A and RNase A-HA decreased their zeta-potentials to 5.4 mV and −21.5 mV, respectively.

These results suggest that the complexation of a lipidoid nanoparticle to a protein was driven mainly by electrostatic interaction.

Finally, as also shown in Table 1, the EC16-80/RNase A-HA nanocomplex unexpectedly exhibited a high protein loading efficiency of 92.7%, as compared to 80.3% exhibited by EC16-80/RNase A nanocomplex.

These results demonstrate that the HA modification of RNase A largely decreased the charge density on the protein, strengthened the complexation of the modified protein with cationic lipidoid nanoparticles, and increased the protein loading efficiency.

Example 3: In Vitro Cytotoxicity of Protein-Loaded Nanocomplexes

Studies were performed using a MTT assay to evaluate the in vitro cytotoxicity of free RNase A-HA, pure EC16-80 nanoparticle, EC16-80/RNase A nanocomplex, and EC16-80/RNase A-HA nanocomplex against A549 cells (high CD44 expression) and MCF-7 cells (low CD44 expression).

To optimize the lipidoid/protein weight ratio for subsequent studies, nanocomplexes having various lipidoid/protein weight ratios (w/w, EC16-80/RNase A-HA=3/1, 2/1, 3/2, 1/1, 3/4, 1/2) were formulated and evaluated using the cytotoxicity assay described above on A549 and MCF-7 cells. When fixing the concentration of RNase A-HA at 4 µg/mL and sequentially increasing the concentration of EC16-80 from 1/2 to 3/1 (the ratio of EC16-80/RNase A-HA), cytotoxicity against A549 cells increased gradually from about 40% to about 70% and cytotoxicity against MCF-7 cells increased gradually from about 40% to about 85%. Notably, each of lipidoid EC16-80 and protein RNase A-HA alone showed negligible cytotoxicity against either cell line. Based on these results, the weight ratio of lipidoid/protein was fixed at 2/1 in the following studies.

Shown in FIG. 2 below are concentration-dependent cytotoxicity of RNase A-HA, EC16-80/RNase A, and EC16-80/RNase A-HA against A549 and MCF-7 cells with and without anti-CD44 antibody pretreatment.

Figure 2:
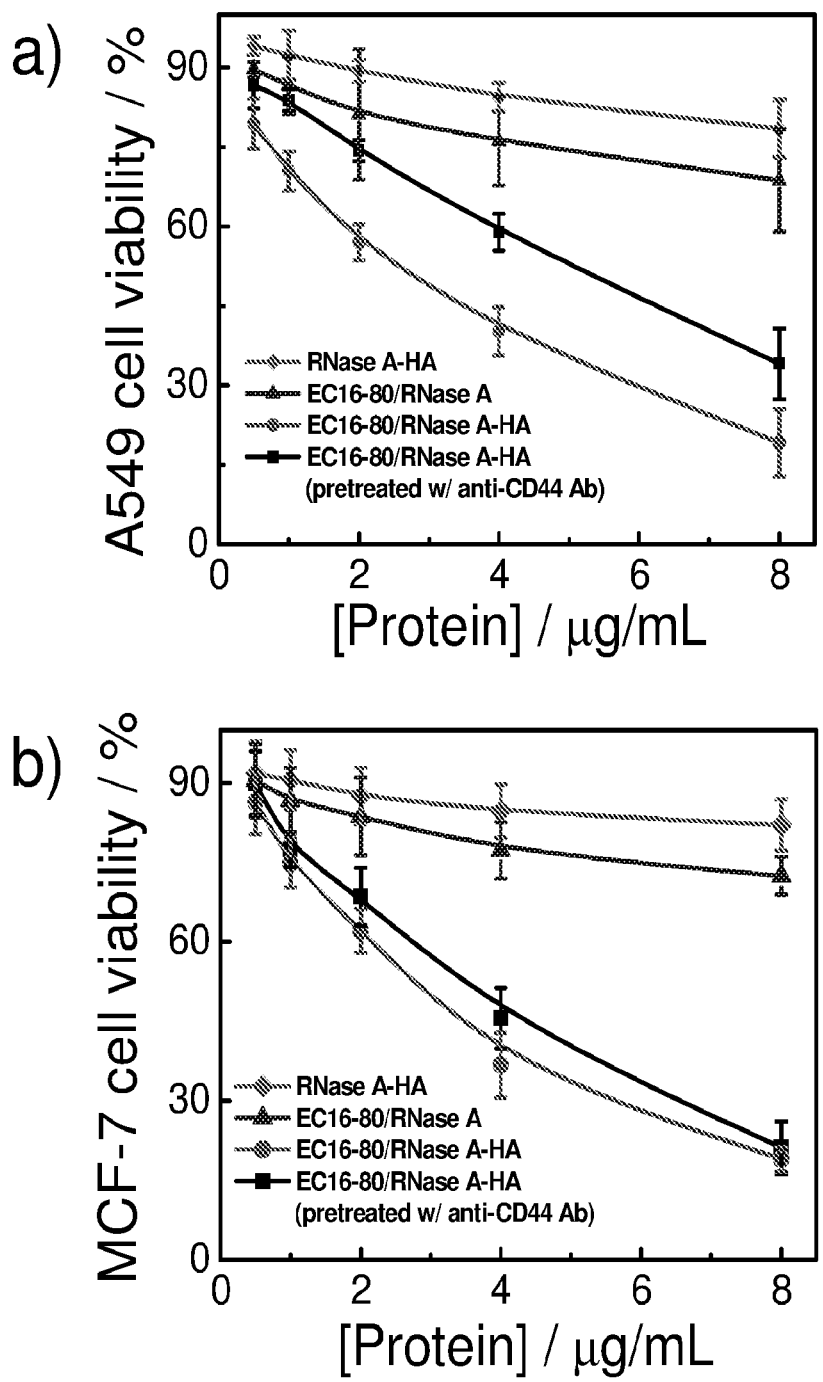
FIG. 2 is a schematic depiction of concentration-dependent cytotoxicity of RNase A-HA, EC16-80/RNase A, and EC16-80/RNase A-HA with and without anti-CD44 antibody pretreatment, against (a) A549 and (b) MCF-7 cell lines.

As shown in FIG. 2, the cytotoxicity of lipidoid/protein nanocomplexes changed in a dose-dependent manner. Both the free RNase A-HA and the EC16-80/RNase A nanocomplex exhibited relatively low cytotoxicity against A549 cells and MCF-7 cells, with cell viabilities greater than 70% under various protein concentrations from 0.5 to 8 µg/mL. On the other hand, EC16-80/RNase A-HA nanocomplex showed significant inhibition of cell proliferation at protein concentrations higher than 2 µg/mL against both A549 and MCF-7 cells. More specifically, at protein concentrations of 2 µg/mL, 4 µg/mL, and 8 µg/mL, EC16-80/RNase A-HA nanocomplex unexpectedly exhibited cell proliferation inhibitions of about 40%, about 60%, and about 80%, respectively, against both A549 cells and MCF-7 cells.

These results demonstrate that HA modified RNase A, i.e. RNase A-HA, was efficiently delivered into cells by a nanocomplex containing an EC16-80 lipidoid nanoparticle and inhibited cell proliferation in a dose-dependent manner.

As HA moieties contained in the nanocomplex could specifically bind to trans-membrane glycoprotein CD44 receptor present on the cell surface, EC16-80/RNase A-HA nanocomplex would be capable of targeting CD44+ cancer cells. As a matter of fact, cytotoxicity of EC16-80/RNase A-HA nanocomplex was unexpectedly found to be significantly decreased against A549 cells (high CD44 expression), but not MCF-7 cells (low CD44 expression), when cells were all pretreated with anti-CD44 antibody.

More specifically, as also shown in FIG. 2 above, the cytotoxicity of EC16-80/RNase A-HA nanocomplex against A549 cells was significantly decreased from about 60% (without anti-CD44 antibody pretreatment) to about 40% (with anti-CD44 antibody pretreatment) at a protein concentration of 4 µg/mL and from about 80% (without anti-CD44 antibody pretreatment) to about 65% (with anti-CD44 antibody pretreatment) at a protein concentration of 8 µg/mL.

By contrast, the cytotoxicity of EC16-80/RNase A-HA nanocomplex against MCF-7 cells was negligibly decreased from about 60% (without anti-CD44 antibody pretreatment) to about 55% (with anti-CD44 antibody pretreatment) at a protein concentration of 4 µg/mL and was not changed at about 80% (with or without anti-CD44 antibody pretreatment) at a protein concentration of 8 µg/mL.

While anti-CD44 antibody pretreatment had a negligible effect on MCF-7 cells having low CD44 expression, it significantly blocked the CD44 receptors expressed on the surface of A549 cell having high CD44 expression, thereby decreasing the intracellular delivery efficiency of EC16-80/RNase A-HA nanocomplex and, as a result, decreasing the cytotoxicity of the nanocomplex.

These results suggest that CD44 receptor-mediated internalization partially contributed to the intracellular delivery of cytotoxic RNase A protein. Thus, use of the lipidoid/protein nanocomplex of this invention for targeted cancer therapy can increase efficacy of protein-based therapeutics and reduce their systemic side effects.

Example 4: Fluorescent Analysis and Cell Imaging

Studies were conducted by using flow cytometry and confocal laser scanning microscopy (CLSM) as follows to evaluate cell internalization efficiencies of free RNase A-HA, EC16-80/RNase A nanocomplex, and EC16-80/RNase A-HA nanocomplex in A549 and MCF-7 cells.

FITC-labeled RNase A (FITC-RNase A) and RNase A-HA (FITC-RNase A-HA) were used in the flow cytometry study. It was observed that A549 cells (high CD44 expression) treated with EC16-80/FITC-RNase A-HA nanocomplex had the highest fluorescent intensity, as compared to free FITC-RNase A-HA and EC16-80/FITC-RNase A. Similar results were observed when MCF-7 cells were used.

These results indicate that (i) a cationic lipidoid nanoparticle was essential for intracellular protein delivery and (ii) HA modification enhanced the cell internalization efficacy of a nanocomplex by strengthening the complexation between the protein and the lipidoid nanoparticle.

Furthermore, when CD44 receptors on the surface of A549 cells were blocked by pretreatment with anti-CD44 antibody, the total fluorescence intensity of A549 cells (high CD44 expression) treated with EC16-80/FITC-RNase A-HA was significantly decreased. By contrast, the antibody pretreatment had a negligible effect on fluorescent intensity of MCF-7 cells (low CD44 expression). These results, consistent with those from the cytotoxicity studies described in EXAMPLE 3, also suggest that blocking CD44 receptor on A549 cell surface can decrease intracellular protein delivery efficacy and lead to less inhibited cell proliferation.

Additionally, CLSM images confirmed that EC16-80/FITC-RNase A-HA nanocomplex had the highest intracellular fluorescence intensity, i.e. highest amount of proteins delivered into cells, as compared to free FITC-RNase A-HA and EC16-80/FITC-RNase A nanocomplex.

In sum, EC16-80/FITC-RNase A-HA nanocomplex of this invention was unexpectedly found to be a highly efficient protein delivery system.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A nanocomplex, comprising:
   a lipid-like nanoparticle; wherein the lipid-like nanoparticle is formed of a cationic lipid-based compound; and
   a modified RNase; wherein the modified RNase is formed of a RNase and an anionic polymer; the anionic polymer is hyaluronic acid;
   wherein the lipid-like nanoparticle binds to the modified RNase via non-covalent interaction to form a nanocomplex having a particle size of about 50 to about 1000 nm.

2. The nanocomplex of claim 1, wherein the cationic lipid-based compound is formed from an electrophile and an amine; wherein the electrophile is an epoxide, an acrylate, or an acrylamide; and the amine is a primary or secondary amine.

3. The nanocomplex of claim 2, wherein the electrophile is an epoxide substituted with $C_1$-$C_{20}$ alkyl or $C_1$-$C_{20}$ heteroalkyl; and the amine is selected from the group consisting of

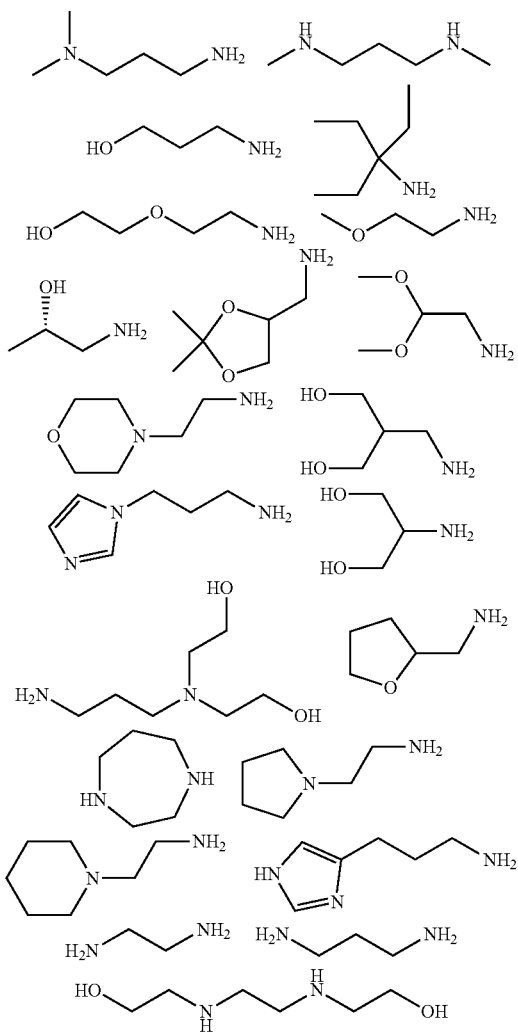

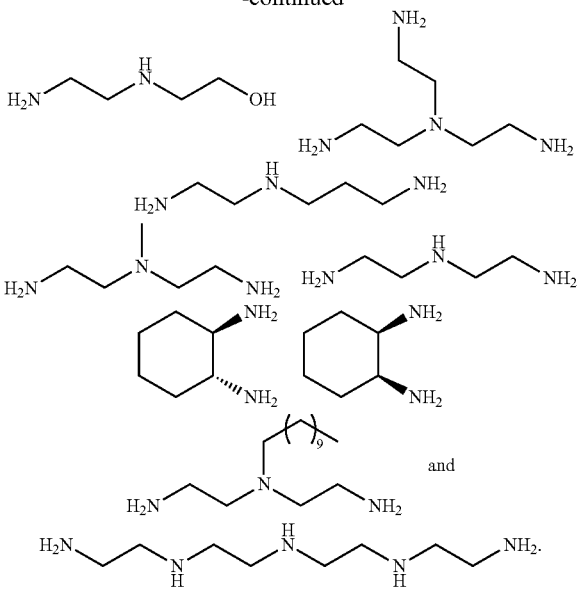

4. The nanocomplex of claim 1, wherein the cationic lipid-based compound is formed from an epoxide substituted with $C_1$-$C_{20}$ alkyl or $C_1$-$C_{20}$ heteroalkyl, and a primary or secondary amine.

5. The nanocomplex of claim 1, wherein the cationic lipid-based compound is formed from

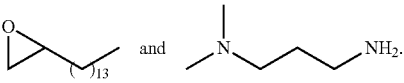

6. A pharmaceutical composition, comprising a nanocomplex of claim 1 and a pharmaceutically acceptable carrier thereof.

7. A method of preparing a nanocomplex of claim 1, comprising:
   activating a hyaluronic acid to form an activated hyaluronic acid;
   conjugating the activated hyaluronic acid to an RNase via covalent bonding to form a modified RNase;
   obtaining a lipid-like nanoparticle formed of a cationic lipid-based compound; and
   bonding the lipid-like nanoparticle to the modified RNase to form a nanocomplex having a particle size of about 50 to about 1000 nm.

8. A method, comprising administering to a subject an effective amount of the nanocomplex of claim 1, wherein the RNase modified protein contained in the nanocomplex is released from the nanocomplex and delivered to cells.

9. The method of claim 8, wherein the subject has cancer.

10. The method of claim 8, wherein the cells to which the modified RNaseprotcin is delivered have elevated CD44 expression compared to healthy cells.

11. The method of claim 10, wherein the subject has cancer.

12. The method of claim 11, wherein the cancer is selected from the group consisting of breast cancer, prostate cancer, ovarian cancer, and leukemia.

* * * * *